United States Patent [19]

Marinak et al.

[11] Patent Number: 4,483,993
[45] Date of Patent: Nov. 20, 1984

[54] PRODUCTION OF POLYCHLORINATED PYRIDINE MIXTURES BY LIQUID PHASE CHLORINATION OF BETA-PICOLINE OR BETA-PICOLINE HYDROCHLORIDE

[75] Inventors: Michael J. Marinak, Kelso; John L. Simonson, Longview, both of Wash.

[73] Assignee: Kalama Chemical, Inc., Kalama, Wash.

[21] Appl. No.: 529,603

[22] Filed: Sep. 6, 1983

Related U.S. Application Data

[63] Continuation-in-part of Ser. No. 483,183, Apr. 8, 1983.

[51] Int. Cl.$^3$ .................. C07D 211/72; C07D 211/84; C07D 213/61
[52] U.S. Cl. ...................................... 546/345
[58] Field of Search ........................................ 546/345

[56] References Cited

U.S. PATENT DOCUMENTS

| | | | |
|---|---|---|---|
| 3,256,167 | 6/1966 | Norton et al. | 546/345 |
| 3,412,095 | 11/1968 | Clark | 546/345 |
| 3,420,833 | 1/1969 | Taplin | 546/345 |
| 3,424,754 | 1/1969 | Taplin | 546/345 |
| 4,184,041 | 1/1980 | Nishiyama | 546/345 |
| 4,205,175 | 5/1980 | Bowden et al. | 546/345 |
| 4,241,213 | 12/1980 | Nishiyama et al. | 546/345 |
| 4,256,894 | 3/1981 | Dietsche et al. | 546/345 |
| 4,331,811 | 5/1982 | Werner et al. | 546/345 |
| 4,429,132 | 1/1984 | Whittaker | 546/345 |

FOREIGN PATENT DOCUMENTS 76860  6/1980  Japan .................................. 546/345

OTHER PUBLICATIONS

Kosorotov et al., Zhurnal Organicheskoi Khimii, vol. 16, No. 10, pp. 2163–2171 (Oct. 1980), (English translation).
Office Action dated Jul. 14, 1980 (Paper No. 5) in Nishiyama et al. U.S. Patent 4,241,213.
Office Action dated Jul. 16, 1979 (Paper No. 3) in Bowden et al. U.S. Patent 4,205,175.
McBee et al., Industrial and Engineering Chemistry, vol. 39, pp. 389–391 (1947).
Ishihara, Chemical Abstracts, 94:83950z (1981).
Wilson et al., Chemical Abstracts, 96:181152b (1982).
Office Action dated Jul. 3, 1980 (Paper No. 11) in Dietsche et al. U.S. Patent 4,256,894.
Declaration Under Rule 132 dated Apr. 24, 1980, by Dietsche in Dietsche et al. U.S. Patent 4,256,894.
Declaration of Craig E. Mixan dated Oct. 29, 1981, located in file history of Werner et al. U.S. Patent 4,331,811.
Werner et al., Chemical Abstracts, 97:92160f (1982).
Ishihara, Chemical Abstracts, 98:143281b (1983).

Primary Examiner—Henry R. Jiles
Assistant Examiner—Robert C. Whittenbaugh
Attorney, Agent, or Firm—Graybeal & Cullom

[57] ABSTRACT

Preparation of high yields of mixtures rich in polychlorinated pyridines by maintaining a chlorine to beta-picoline weight ratio of greater than about 5:1 when reacting chlorine and beta-picoline or beta-picolie hydrochloride non-catalytically in the liquid phase at temperatures of at least about 190° C., the reactants being contained in a well mixed diluent producing less than one mole of hydrogen chlorine per mole of diluent by reaction with the chlorine in the indicated temperature range. Chlorination of the beta-picoline or beta-picoline hydrochloride in a primary reactor is followed by selective further chlorination thereof in finishing reactor means at a temperature of at least about 190° C. to obtain high yields of desired final products useful as intermediates in the formation of herbicides and the like. Like further chlorination to obtain such final products is also applicable to mixtures rich in monochloro-, dichloro-, and trichloro-3-trichloromethyl pyridines produced by other processes.

37 Claims, 1 Drawing Figure

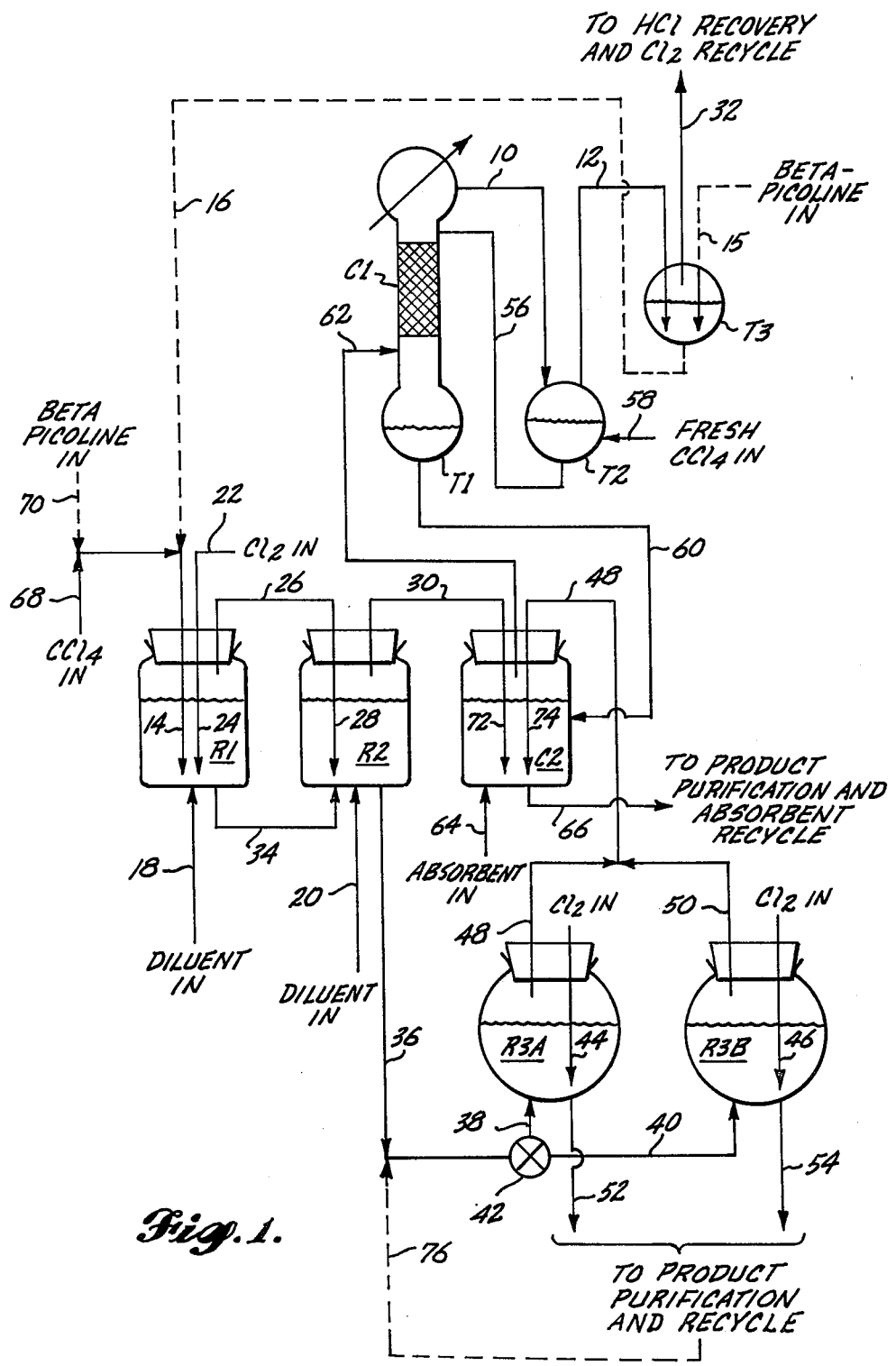

PRODUCTION OF POLYCHLORINATED PYRIDINE MIXTURES BY LIQUID PHASE CHLORINATION OF BETA-PICOLINE OR BETA-PICOLINE HYDROCHLORIDE

CROSS REFERENCE TO RELATED APPLICATION

This application is a continuation-in-part of our copending U.S. application Ser. No. 483,183 filed Apr. 8, 1983 and entitled "Production Of Polychlorinated Pyridine Mixtures By Liquid Phase Chlorination Of Beta-Picoline Or Beta-Picoline Hydrochloride."

BACKGROUND OF THE INVENTION

1. Field of the Invention

The present invention relates to preparation of polychlorinated pyridine mixtures by direct liquid phase chlorination of beta-picoline or beta-picoline hydrochloride. Typical of the products produced are 2,3,6-trichloro- and 2,3,5,6-tetrachloro pyridine; and 3-chloro-, 5-chloro-, 6-chloro-, 2,6-dichloro-, 5,6-dichloro- and 2,5,6-trichloro-3-trichloromethyl pyridine. These products have utility, for example, as intermediates for herbicides and insecticides. A further aspect of the present invention relates to further non-catalytic chlorination of mixtures rich in 2-chloro-and 6-chloro-3-trichloromethyl pyridine to form 2,6-dichloro-3-trichloromethyl pyridine and/or 2,3,6-trichloro pyridine, and the further non-catalytic chlorination of mixtures rich in 5-chloro-3-trichloromethyl pyridine and 5,6-dichloro-3-trichloromethyl pyridine to form 2,5,6-trichloro-3-trichloromethyl pyridine and/or 2,3,5,6-tetrachloro pyridine.

Yet another aspect of the invention relates to catalytically chlorinating mixtures rich in 6-chloro- and mixtures rich in 2,6-dichloro-3-trichloromethyl pyridine to form mixtures rich in 5,6-dichloro- and 2,5,6-trichloro-3-trichloromethyl pyridine. The mixtures rich in 5,6-dichloro- and 2,5,6-trichloro-3-trichloromethyl pyridine may then be non-catalytically chlorinated to form mixtures rich in 2,3,5,6-tetrachloro pyridine.

Still another aspect relates to the formation of 2,3,5,6-tetrachloro pyridine from both catalytic and non-catalytic chlorination of 2,3,6-trichloro pyridine.

DESCRIPTION OF THE PRIOR ART

The utility of 2,3,5,6-tetrachloropyridine as an intermediate to insecticidal compositions is set forth in Dietsche et al U.S. Pat. No. 4,256,894. The conversion of 2,3,6-trichloro pyridine to the more desirable 2,3,5,6-tetrachloro pyridine by liquid phase ferric chloride-catalyzed chlorination is also taught by Dietsche et al U.S. Pat. No. 4,256,894.

To the best of applicants' knowledge, there is no known process for liquid phase chlorination of beta-picoline or beta-picoline hydrochloride to yield the valuable chlorinated intermediates 2-chloro-, 5-chloro-, 6-chloro-, 5,6-dichloro-, 2,6-dichloro- and 2,5,6-trichloro-3-trichloromethyl pyridine and 2,3,6-trichloro- and 2,3,5,6-tetrachloro pyridine.

Vapor phase processes for chlorination of beta-picoline or beta-picoline hydrochloride, all operating in the temperature range of from about 300° C. to about 500° C., are known. Clark U.S. Pat. No. 3,412,095 describes a vapor phase beta-picoline chlorination process yielding 3-monochloromethyl pyridine. Bowden et al in U.S. Pat. No. 4,205,175 describes a vapor phase chlorination process which yields a mixture of 2-chloro-and 6-chloro-3-trichloromethyl pyridine. Utility of these intermediates to produce herbicidal compositions is also described. Nishiyama et al U.S. Pat. No. 4,241,213 also describes a vapor phase chlorination process to yield mixtures rich in 6-chloro-3-trichloromethyl pyridine. This compound is particularly useful as an intermediate for herbicidal compositions.

Nishiyama U.S. Pat. No. 4,184,041 describes the utility of 5,6-dichloro-3-trichloromethyl pyridine in the production of herbicidal compositions.

SUMMARY OF THE INVENTION

It has been discovered that high yields of mixtures rich in chlorinated picolines/pyridines may be achieved by non-catalytically chlorinating beta-picoline or beta-picoline hydrocholoride in a diluent in the liquid phase at temperatures of at least about 190° C. while maintaining strong agitation and a feed ratio of chlorine to beta-picoline of at least about 5:1 by weight while feeding the chlorine and beta-picoline or beta-picoline hydrochloride to the reaction mass in a primary reactor. The beta-picoline can be dissolved in carbon tetrachloride or fed full strength into the reactor. It !s desirable to have a supply of carbon tetrachloride available for flushing the feed line in the event of a shutdown because stagnant beta-picoline would otherwise tend to degrade in and plug the feed line. If beta-picoline hydrochloride is the desired feed form, it is fed directly through a sparger into the bottom of the primary reactor. After the beta-picoline or beta-picoline hydrochloride has been partially chlorinated in the primary reactor, the polychloro picoline is subjected to further chlorination in one or more secondary reactors for such times and temperatures as appropriate to maximize the yield of the desired end product or products.

The percent of volatiles realized by liquid phase chlorination according to the present invention is dependent upon the diluent composition, the extent of mixing of the reactants and diluent, the picoline feed rate to reaction mass volume, the weight ratio of chlorine-to-picoline being fed, and the chlorine partial pressure, which influences chlorine solubility. The composition of the diluent media in which the reaction proceeds is important in practice of this invention, to secure good yields of the desired volatile chlorinated beta-picolines. Its function in this invention is quite different from the initiator charge described in Taplin U.S. Pat. No. 3,424,754, which deals with alpha-picoline liquid phase chlorination. In U.S. Pat. No. 3,424,754, the initiator charge has the function of evolving HCl when contacted with chlorine at the reaction temperature in order to react with alpha-picoline to form picoline hydrochloride. In the present invention, the diluent's function is to be reactively less competitive for the chlorine dissolved in it and to help remove the heat of reaction evolved by the chlorination of the beta-picoline.

Examples of some compounds usable as diluents in the practice of the present invention, in that they generate one mole or less of HCl per mole of compound when contacted with chlorine under the reaction conditions of the present invention, are: 3-chloro-, 5-chloro-, 6-chloro-, 5,6-dichloro-, 3,5-dichloro-, 3,6-dichloro-, 3,4,5-trichloro- and 3,5,6-trichloro-2-trichloromethyl pyridine, 2-chloro-, 6-chloro-, 2,6-dichloro-3-trichloromethyl pyridine, and 2,3,6-trichloro-, 2,3,5,6-tetrachloro-, and 2,3,4,5,6-pentachloro pyridine, and mixtures thereof. This list is not meant to be exhaustive of all possible diluent constituents but is illustrative of compounds useful for the purpose. The diluent may be the chlorinated pyridine/picoline products from a previous reaction which meet the above criteria and is high in volatiles content.

In the practice of the present invention, an excess of chlorine is fed relative to that needed for the beta-picoline and beta-picoline hydrochloride chlorination, which excess provides additional agitation and hence better mixing, and also a higher chlorine partial pressure which increases the chlorine solubility in the reaction media. A chlorine to beta-picoline weight ratio of at least about 5:1 is needed. As the temperature increases in excess of 200° C., the weight ratio of chlorine to beta-picoline fed needs to be higher in order to achieve the high yields of the desired volatile chloro-picolines. This is necessary because chlorine reacts more rapidly with the beta-picoline or beta-picoline hydrochloride as the temperature increases and therefore the chlorine dissolved in the reaction medium must be more rapidly replaced. This is accomplished by increasing the rate of chlorine addition relative to the beta-picoline flow rate which increases the chlorine partial pressure and hence its mole fraction in the liquid reaction medium. Gas solubilities tend to decrease with rising temperature, but an increase in system pressure increases the chlorine solubility.

The beta-picoline or beta-picoline hydrochloride feed is to be controlled relative to the reaction volume so no more than about 10% by volume of light phase accumulates relative to the chlorinated picoline phase at temperatures in excess of about 190° C. Potential decomposition products can result above this temperature in the absence of cooling and excess chlorine. Since beta-picoline hydrochloride and the diluent are somewhat immiscible and of different densities, good mixing is necessary in order to achieve dispersion of chlorine and beta-picoline or beta-picoline hydrochloride into the diluent.

Controlling these variables results in the high yields of volatile polychlorinated beta-picolines in the liquid phase at temperatures in excess of 190° C.

Care must be taken to ensure that metallic impurities, such as iron, copper, aluminum and other Lewis Acid type metals, are excluded from the reaction mass, as they will cause different reactions in the chlorination that may not be desirable.

We have also discovered that the chloro-picolines can be further chlorinated non-catalytically, at predictable functions of time vs. temperature, to give other useful intermediates. For example, when subjected to further non-catalytic chlorination in liquid phase at high temperature, 5-chloro-3-trichloromethyl pyridine goes to 5,6-dichloro-3-trichloromethyl pyridine. Similarly 6-chloro-3-trichloromethyl pyridine non-catalytically chlorinates to 2,6-dichloro-3-trichloromethyl pyridine as does 2-chloro-3-trichloromethyl pyridine. The process can be interrupted at this stage and these two main components, namely, 5,6-dichloro-3-trichloromethyl pyridine and 2,6-dichloro-3-trichloromethyl pyridine, may be separated out, or, if chlorination is continued, 5,6-dichloro-3-trichloromethyl pyridine goes to 2,5,6-trichloro-3-trichloromethyl pyridine and on still further chlorination to 2,3,5,6-tetrachloro pyridine, which has great utility as an intermediate in insecticidal compositions. 2,6-Dichloro-3-trichloromethyl pyridine can be chlorinated non-catalytically further to 2,3,6-trichloro pyridine. 2,3,6-Trichloro pyridine also can be chlorinated with or without ferric chloride catalyst to 2,3,5,6-tetrachloro pyridine. The process can be selectively controlled to realize a very high yield of 2,3,5,6-tetrachloro pyridine, or the yield of 5,6-dichloro-3-trichloromethyl pyridine and 6-chloro-3-trichloromethyl pyridine, both of which have utility as intermediates for herbicides, can be maximized by not chlorinating as long.

Mixtures rich in 6-chloro-3-trichloromethyl pyridine can be chlorinated catalytically to mixtures rich in 2,5,6-trichloro-3-trichloromethyl pyridine. Mixtures rich in 2,6-dichloro-3-trichloromethyl pyridine can be chlorinated catalytically to mixtures rich in 2,5,6-trichloro-3-trichloromethyl pyridine. Mixtures rich in 2,5,6-trichloro-3-trichloromethyl pyridine can be chlorinated non-catalytically to mixtures rich in 2,3,5,6-tetrachloro pyridine.

BRIEF DESCRIPTION OF THE DRAWINGS

FIG. 1 is a schematic diagram of a reaction system for practicing the process of the present invention on a continuous batch basis.

DESCRIPTION OF THE PREFERRED EMBODIMENTS

EXAMPLE 1

FIG. 1 schematically illustrates a continuous batch type reaction system for producing mixtures rich in polychlorinated pyridine/picolines according to the present invention. Primary reactor R1, secondary reactor R2, and absorber C2 are suitably glass of cylindrical configuration, electrically heated and each about 1 liter in volume, and with an inside diameter of 4 inches and an inside height of 7 inches. Finishing reactors R3A and R3B are glass, spherical, electrically heated and about 1 liter in volume. Water-cooled scrubber column C1 is suitably of cylindrical design, 1½ inches in diameter, containing as packing some 18 inches of ¼ inch glass rings.

Scrubber column C1 includes a holding tank or reservoir T1 and the overhead vapor from column C1 is delivered through vent line 10 to disengaging tank T2 in which the carbon tetrachloride collects, with the chlorine and hydrogen chloride evolving from column C1 being delivered by vent line 12 and sparged into hydrochlorination tank T3. For startup, beta-picoline hydrochloride, suitably previously prepared conventionally, as by sparging anhydrous HCl into a pool of beta-picoline maintained between 80° C. and 100° C. until saturated with HCl, is charged to hydrochlorination tank T3 and beta-picoline hydrochloride is withdrawn from tank T3 and delivered to bottom discharging sparger 14 in reactor R1 through line 16. An alternate startup mode involves feeding beta-picoline dissolved in carbon tetrachloride through lines 68 and 70 thence into line 14, generating hydrogen chloride which is vented to hydrochlorination tank T3. For startup, also, primary reactor R1 was charged through charge line 18 with 1000 grams of diluent, consisting of chlorinated pyridine from a previous reaction (suitably comprising about 22.4% 6-chloro-, 48.9% 5,6-dichloro-, 27.3% 3,6-dichloro-, and 4.1% 4,6-dichloro-2-trichloromethyl pyridine by weight). 406 grams of like diluent material was also charged to secondary reactor R2 through charge line 20. 453 grams of a suitable absorbent was charged through charge line 64 to absorber C2, the composition of the absorbent selected for this example being 66.7% 6-chloro-, 15.2% 5,6-dichloro-, 1.8% 3,6-dichloro-2-trichloromethyl pyridine, and 4.9% 2,6-dichloro-, 4.9% 2,3,5,6-tetrachloro-, and 1.1% 2,3,4,5,6-pentachloropyridine, and 2.7% 5,6-dichloro-, 1.8% 2,6-dichloro-3-trichloromethyl pyridine, by weight.

The absorbent charged to C2 needs to have a melting point of less than 80° C. and substantial solubility with carbon tetrachloride. Its purpose is to absorb higher melting chlorinated pyridines, e.g. those with melting points greater than 90° C., namely, 2,3,5,6-tetra- and 2,3,4,5,6-pentachloro pyridine. If these higher melting point chloropyridines were allowed to enter the scrubber column C1 in substantial quantity, they would tend to plug the column packing. The refluxing carbon tetrachloride in scrubber column C1 tends to concentrate the entrained chloropyridines that enter it in the bottom tank T1 thereof, and keep the overhead vapors substantially free of chlorinated pyridines which would otherwise plug the vapor outlet 10. Some typical examples which meet the criteria of suitable absorbent materials for absorber C2 are 6-chloro-, 5,6-dichloro-, 3,6-dichloro-, 3,5-dichloro-2-trichloromethyl pyridine, and mixtures thereof.

The operational startup sequence is that of introducing the diluent to the primary and secondary reactors, then initiating chlorine flow, then heating the reactors to desired reaction temperature, then initiating the beta-picoline or beta-picoline hydrochloride flow. By this procedure, the beta-picoline or beta-picoline hydrochloride only sees excess chlorine in the reactors and degradation thereof to nonvolatiles is avoided. Once reactors R1 and R2 were charged, external heat was applied and the temperature of primary reactor R1 thereof was maintained at 230° C., with secondary reactor R2 being maintained at 150° C. and absorber C2 maintained at 140° C. Chlorine gas from a suitable pressurized source was delivered to the reactor R1 through feed line 22 and bottom placed sparger 24 at a flow rate of 440 grams per hour. The flow rate of beta-picoline hydrochloride sparged into reactor R1 through bottom placed sparger 14, the discharge stream of which is closely adjacent (with about ⅛ inch spacing) to the discharge stream of chlorine sparger 24, was maintained at a rate equivalent to 29 grams beta-picoline per hour, amounting to a chlorine to picoline feed ratio of about 15:1.

As will be understood, the beta-picoline hydrochloride fed to primary reactor R1 releases hydrogen chloride from both the reaction with the chlorine and the decomposition of the hydrochloride salt. This hydrogen chloride along with excess chlorine is vented from reactor R1 through vent line 26 and sparged into the charge in secondary reactor R2 through bottom discharging sparger 28, the overhead vapor including hydrogen chloride and excess chlorine being vented from reactor R2 and delivered through line 30 to absorber C2, thence through line 62 to scrubbing column C1, thence through line 10 and line 12 to hydrochlorinating tank T3, the vapor flow from which passes through line 32 to hydrogen chloride and chlorine gas recovery means, known per se, for recycling of the chlorine gas to the process and recovery of the hydrogen chloride, as desired. Once hydrogen chloride gas is being generated and is passing through the system to hydrochlorination tank T3, the beta-picoline feed into tank T3 through line 15 can be started if that is the desired feed mode.

Secondary reactor R2 is only partially charged with diluent at startup. This is for the reason that, as the volume of the reaction mass in reactor R1 increases in the course of the reaction, a portion of the reaction mass is moved from reactor R1 to reactor R2 (by volatilization and entrainment) through line 26 and through discharge line 34 for further chlorination in reactor R2. The temperature in secondary reactor R2 influences the degree of continued chlorination. In this example the relatively low temperature of 150° C. serves to quench the reaction occurring in primary reactor R1 and to slow the rate of chlorination. A higher temperature in secondary reactor R3, such as a temperature greater than 200° C., would continue the chlorination process at a higher rate than occurs at 150° C. In this example, reactors R3A and R3B were chosen to take the reaction to the desired degree of chlorination by operating at 210° C. for 12 hours.

When the liquid volume in secondary reactor R2 increases to the point where the reactor R2 is filled to its operating level, further increase in liquid volume is taken care of by progressively discharging the excess through line 36 to either finishing reactor R3A through line 38, or to finishing reactor R3B through line 40, depending on the setting of valve 42.

Chlorination to process end point is completed in either reactor R3A or reactor R3B by continued introduction of chlorine gas through bottom discharging sparger 44 or 46, with continued heating of the reactors R3A or R3B to a desired temperature for a desired time to yield the desired product distribution, e.g. a temperature of 210° C. and a time of twelve hours, in this selected example. Chlorine and hydrogen chloride vapor takeoff from reactors R3A and R3B is delivered through vent lines 48, 50 to absorber C2 through sparge line 74, thence to scrubber column C1.

Chlorinated reaction product is withdrawn from the reactors R3A and R3B through respective discharge lines 52, 54, with the product going to product purification means known per se, such as a vacuum fractional distillation column. Liquid discharge from holding tank T2 is delivered to scrubber column C1 through line 56 to return carbon tetrachloride to the column C1, with makeup of carbon tetrachloride from an appropriate supply if necessary, as indicated at 58. The liquid phase fraction collecting in bottom tank T1 of the scrubber column C1 is returned to absorber C2, as indicated at line 60.

Finishing reactors R3A and R3B can be smaller or larger than reactors R1 and R2, depending on the desired residence time to complete the chlorination reaction. For example, with a reaction temperature of 230° C. and a residence time of 12 hours in the primary reactor R1 and a reactor temperature of 150° C. and a residence time of 12 hours in the secondary reactor R2, the time required to complete the reaction in reactor R3A or in reactor R3B is about 12 hours at 210° C. temperature. The controlling factor determining reaction time in reactor R3A or reactor R3B is the maximum concentration of the desired product. If the principal desired product is 5,6 dichloro-3-trichloromethyl pyridine, additional chlorination in R3A or R3B would be required for maximum recovery. If the principal desired product is 6-chloro-3-trichloromethyl pyridine, less time would be required in R3A or R3B. Correspondingly, additional time would be required to maximize the concentration of 2,3,6-trichloro pyridine in R3A or R3B. In this first example, it has been assumed that a mixture of end product compounds, with each compound present in substantial proportion, was desired, and to this end the composition of the end product obtained in R3A and R3B comprised 11.7% 2,3,6-trichloro pyridine, 24.4% 6-chloro-3-trichloromethyl pyridine, and 16.1% 5,6-dichloro-3-trichloromethyl pyridine, by weight. Further, product purification and recycle to R3A or R3B for further chlorination, as indicated at 76, can convert the 5-chloro-3-trichloromethyl pyridine to 5,6-dichloro-3-trichloromethyl pyridine and 2-chloro- and 2,6-dichloro-3-trichloromethyl pyridine to 2,3,5-trichloro pyridine.

Excess chlorine, hydrogen chloride, and some volatile corrosive chloro-picoline hydrochlorides and entrained chlorinated pyridines, some of which have melting points in excess of 100° C., are transferred to secondary reactor R2 from primary reactor R1 by heated vent line 26 and bottom discharging sparger 28, with the volatile hydrochlorides being absorbed and reacted further in secondary reactor R2. These hydrochlorides are very corrosive and tend to form solids on condenser surfaces that are in the 30° C. to 100° C. temperature range, the operating temperature range of scrubber column C1 and, along with the high melting chloropyridines, would cause a plugging problem in column C1 if passed directly from primary reactor R1 to the scrubber column C1. Their absorption and further reaction in secondary reactor R2 help eliminate such plugging problems and absorber C2 completely eliminates the high melting chloropyridines in the vent line 62 to column C1. The excess chlorine, hydrogen chloride, and entrained products passing to column C1 through absorber C2 vent line 62 are there scrubbed with carbon tetrachloride discharged to column C1 through line 56. The entrained chlorinated pyridine products buildup in tank T1 and the liquid level therein is controlled by recycling the excess liquid back to absorber C2 through discharge line 60. When the level in absorber C2 reaches the operating level, processing of the excess material is begun through line 66 for removal of the high melting chloropyridine reaction products from the absorber material. These chlorinated pyridine products are removed from the absorbent material by vacuum distillation. Process absorbent is then recycled back to C2 through line 64.

As will be apparent, finishing reactors R3A and R3B are operated in a batch manner, permitting one to be on line while the other is having the chlorinated product removed or is being filled from secondary reactor R2. Analysis of the reaction mass in the on line reactor R3A or R3B for maximum concentration of the desired chloropyridine(s) indicates when the reaction is finished. When this occurs the contents of the on line reactor R3A or R3B are pumped through the respective discharge lines 52 or 54 to the purification section of the system, conventional per se.

The residence time in each reactor R1, R2 and R3A or R3B typically varies from about 5 to about 40 hours, and the total cycle time in the reactors is about 10 to 120 hours. From the previously described feed and reaction conditions set forth in Example 1, 75 grams per hour of product was obtained that contained about 14.1% 5-chloro-, 24.4% 6-chloro-, 6.3% 2-chloro-, 16.1% 5,6-dichloro-, and 9.8% 2,6-dichloro-3-trichloromethyl pyridine, by weight. In addition, 11.7% 2,3,6-trichloro pyridine was present. The volatiles content of the reaction mass was greater than 96%. As known per se, 2,3,6-trichloro pyridine can be separated and processed further through ferric chloride catalyzed liquid phase chlorination to 2,3,5,6-tetrachloro pyridine, such as described in Dietsche et al U.S. Pat. No. 4,256,894. In this example, also, the total residence time was about 21 hours. In practice of the invention appropriate variation in residence time is determinable on a predictable basis, taking into consideration the product composition desired, and the reactor pressure and reactor temperature. In addition, the quantity of diluent recycled to the reactors may also be varied to vary the residence time. In any event, as earlier indicated, the feed rate of beta-picoline or beta-picoline hydrochloride relative to the reaction volume is to be controlled so that no greater than about 10% by volume of lighter phase (undiluted picoline hydrochloride) exists in the reaction mass.

The gases in vent line 32 from hydrochlorination tank T3 are predominantly excess chlorine and hydrogen chloride, which stream can be separated or purified by a number of conventional techniques such as absorption of the hydrogen chloride in water, or drying the chlorine and compressing the chlorine gas for recycle, or fractional distillation.

EXAMPLE 2

Utilizing the same reaction system shown in FIG. 1 and described in Example 1, reactors R1 and R2 were respectively charged with 928 grams and 635 grams of chlorinated picoline diluent from a previous reaction. Absorber C2 was charged with 585 grams of the same material. The composition of the diluent was 4% pentachloropyridine, 54% 6-chloro-, 15% 6-dichloro-, and 2% 4,6-dichloro-2-trichloromethyl pyridine, and 6.3% 6-chloro-, 2% 2-chloro-, 1.5% 5,6-dichloro- and 1.5% 2,6-dichloro-3-trichloromethyl pyridine, by weight. Chlorine at a flow rate of 440 grams per hour was sparged into reactor R1 and reactors R1 and R2 were heated to temperatures of 210° C. and 150° C. respectively. Absorber C2 was maintained at 140° C. Beta-picoline was then sparged into reactor R1 through sparger 14 after being premixed with about an equal volume of carbon tetrachloride. The beta-picoline feed was at a rate equivalent to about 20 grams beta-picoline per hour. The average residence time of the reaction mass in each of the reactors R1 and R2 was about 12 hours. Chlorination of the effluent from reactor R2 was continued in reactor R3A for 9 hours at 160° C. and then for 5 hours at 190° C. The resulting reaction product contained about 21% 5,6-dichloro-3-trichloromethyl pyridine by weight, and the volatile content of the reaction mass was greater than 98%.

The analyses of the reaction products obtained in Examples 1 and 2 are given in the following Table ONE.

TABLE ONE

| Compound | Example 1 | Example 2 |
|---|---|---|
| 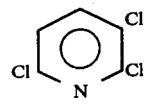 | 11.7% by wt. | |
| 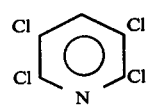 | 3.4 | |

TABLE ONE-continued

| Compound | Example 1 | Example 2 |
|---|---|---|
| 2-Cl, 6-CCl₃ pyridine | 14.1 | |
| 2-Cl, 3-CCl₃ pyridine | 24.4 | 3.0% by wt. |
| 3-CCl₃, 4-Cl pyridine | 6.3 | 3.6 |
| 2,3-diCl, 6-CCl₃ pyridine | 16.1 | 21.4 |
| 2,4-diCl, 3-CCl₃ pyridine | 9.8 | 12.5 |
| 2,4-diCl, 3-CHCl₂ pyridine | | 29.1 |
| 2,4,6-triCl, 3-CCl₃ pyridine | | 25.4 |

EXAMPLES 3 through 7

Examples 3 through 7 serve to illustrate some of the process variables which can occur in practice of the present invention, and for such purpose were conducted as simplified batch processes. A chlorination reactor comprising a 1000 ml spherical glass reactor, heated by an electric heating mantle, was equipped with two sparge tubes and a line which was vented through a 5000 ml glass knockout pot to a caustic scrubber. The spargers were bottom placed and closely spaced (2 centimeters apart) and the respective feed lines to the spargers were fed through rotometers and flow controlled through respective needle valves, one being supplied from the source of chlorine gas, and the other supplied from a source of beta-picoline (Examples 3 and 4) or beta-picoline hydrochloride (Examples 5-7). In each run, the procedure followed was the same except for the variables investigated, namely, diluent composition, temperature, chlorine-to-picoline feed ratio, residence time, and picoline flow rate relative to reaction mass volume. In Example 3, which is illustrative, the reactor was charged with 715 grams of diluent, the composition of which is given in the following TABLE TWO, and chlorine feed was initiated through the chlorine sparger at the rate of 380 grams per hour and the charge heated to a temperature of 235° C. Beta-picoline dissolved in an equal volume of carbon tetrachloride was then sparged into the reactor at the rate of about 28 grams per hour for a period of 5 hours. The weight ratio of chlorine to the beta-picoline being fed during the reaction was about 13.5:1. Chlorine feed was continued at the rate of 380 grams per hour for 9 more hours at a temperature of 210° C. after the picoline feed was discontinued. The reaction process parameters are tabulated in the following TABLE THREE. The gross weight of the resulting reaction product was 1065 grams, indicating a net production of 350 grams of product. The product was a clear tractable fluid, with a volatiles proportion of greater than 98%, as measured by internal standard gas chromatography. The constituency of the product was as tabulated in TABLE THREE.

As indicated, additional runs, designated Examples 4, 5, 6 and 7 involved the diluents set forth in TABLE TWO, the parameters set forth in TABLE THREE and produced reaction products comprising the compounds set forth in TABLE FOUR.

TABLE TWO

| | DILUENT COMPOSITION | | | |
|---|---|---|---|---|
| Compound | Examples 3 & 4 | Example 5 | Example 6 | Example 7 |
| 2,6-diCl pyridine | | 2.2% by wt. | 2.5% by wt. | |
| 2,3,6-triCl pyridine | | 1.7 | 1.0 | |
| 2,3,4,6-tetraCl pyridine | 3.0% by wt. | 2.1 | 2.1 | |
| 2-Cl, 6-CCl₃ pyridine | 73.0 | 61.1 | 77.0 | 17.4% by wt. |

TABLE TWO-continued

| Compound | DILUENT COMPOSITION | | | |
|---|---|---|---|---|
| | Examples 3 & 4 | Example 5 | Example 6 | Example 7 |
| 2,3-dichloro-6-(trichloromethyl)pyridine | 17.0 | 9.2 | 10.7 | 51.6 |
| 3,5-dichloro-2-(trichloromethyl)pyridine | 2.3 | 0.6 | 1.0 | 22.3 |
| 3,5,6-trichloro-2-(trichloromethyl)pyridine | 2.0 | 0.6 | 1.0 | 1.4 |
| 3,4,5-trichloro-2-(trichloromethyl)pyridine | 1.0 | | 1.0 | |
| 5-chloro-2-(trichloromethyl)pyridine | | 1.8 | 1.6 | |
| 3,5-dichloro-2-(trichloromethyl)pyridine (isomer) | | 7.3 | | |
| 2-chloro-3-(trichloromethyl)pyridine | | 2.9 | | |
| 2,5-dichloro-3-(trichloromethyl)pyridine | | 7.4 | | |

TABLE THREE

| | Ex. 3 | Ex. 4 | Ex. 5 | Ex. 6 | Ex. 7 |
|---|---|---|---|---|---|
| Initial Reactor Temp | 235° C. | 245° C. | 250° C. | 235° C. | 195° C. |
| Diluent charge | 715 gms | 470 gms | 934 gms | 825 gms | 677 gms |
| Feed Form | beta picoline/CCl₄ | beta picoline/CCl₄ | beta picoline/hydro-chloride | beta picoline/hydro-chloride | beta picoline/hydro-chloride |
| Cl₂ Flow Rate | 380 gms/hr | 380 gms/hr | 440 gms/hr | 440 gms/hr | 440 gms/hr |
| Beta-Picoline flow rate (as beta-picoline) | 28 gms/hr | 29 gms/hr | 25 gms/hr | 9 gms/hr | 4.9 gms/hr |
| Cl₂:beta-picoline ratio | 13.5:1 | 13:1 | 17:1 | 49:1 | 9:1 |
| (by weight) Reaction Time with both Cl₂ and beta-picoline feeds | 5 hrs | 5 hrs | 1.50 hrs | 6 hrs | 5 hrs |
| Additional reaction time and temp. with Cl₂ feed only | 9 hrs @ 210° C. | | 9 hrs @ 160° C. + 5 hrs @ 190° C. | 2 hrs @ 190° C. | 6 hrs @ 210° C. |
| Amt. of product produced | 350 gms | 355 gms | 93 gms | 133 gms | 602 gms |
| Volatility of produced product | >98% | 92% | 99% | 99% | 99% |

TABLE FOUR

| Compound | Example 3 | Example 4 | Example 5 | Example 6 | Example 7 |
|---|---|---|---|---|---|
| 2,3,6-trichloropyridine | 25% by wt. | | | 3.5% by wt. | |
| 2,3,5,6-tetrachloropyridine | | | | 3.0 | |
| 2-Cl-5-CCl₃ pyridine (Cl, CCl₃) | 7.5 | 7.1% by wt. | | | 15.8% by wt. |
| 2-Cl-5-CCl₃ pyridine (Cl, CCl₃) | 5.4 | 45.7 | 20.0% by wt. | 55.3 | 7.6 |
| 2-CCl₃-3-Cl pyridine | | 15.0 | 21.0 | 14.4 | 9.5 |
| 2,6-diCl-3-CCl₃ pyridine | 6.8 | 6.4 | 10.0 | 2.0 | 23.9 |
| 2-Cl-3-CCl₃ pyridine | 42.7 | 4.7 | 49.0 | 38.9 | 12.1 |
| 2,6-diCl-5-CCl₃ pyridine | 10.5 | | | | |
| 2,6-diCl-3-CHCl₂ pyridine | 2.0 | 2.0 | | | |
| 2,4,6-triCl-3-CCl₃ pyridine | | | | | 31.1 |

An important aspect of the present invention is the discovery that further liquid phase chlorination of certain monochloro and dichloro-3-trichloromethyl pyridines, in liquid phase and at a temperature of at least about 190° C., can be effected in a chlorinating reactor, such as finishing reactors R3A and R3B, to realize valuable dichloro- and trichloro-3-trichloromethyl pyridines and trichloro and tetrachloro pyridines. As will be apparent, this aspect of the invention is applicable to effluent mixtures from reactor R2 in the foregoing examples, and also to monochloro and dichloro-3-trichloromethyl pyridines and mixtures thereof prepared by other processes, such as the chlorinated beta-picolines produced by the vapor phase processes disclosed in Bowden et al U.S. Pat. No. 4,205,175 (2-chloro- and 6-chloro-3-trichloromethyl pyridine), as well as Nishiyama U.S. Pat. No. 4,241,213 (6-chloro-3-trichloromethyl pyridine).

The following Examples 8 through 17 are presented to illustrate batch-type chlorination products obtained by continued liquid phase chlorination of mixtures rich in monochloro, dichloro-, and trichloro-3-trichloromethyl pyridines, such as those obtained in the effluent mixtures from reactor R2 by the process of the present invention, or which may be otherwise obtained or available from other chlorination processes.

In Examples 8-11, sixty grams per hour of chlorine were sparged into the bottom of a heated 250 cc spherical glass reactor.

EXAMPLE 8

In Example 8 shown in TABLE FIVE, 100 grams of a mixture rich in 6-chloro- and 2-chloro-3-trichloromethyl pyridine were chlorinated in the liquid phase at 190° C. After two hours, the reactor was sampled and a significant decrease in the concentrations of the 6-chloro- and 2-chloro-3-trichloromethyl pyridine was noted, i.e. 15.6% decreased to 9.6% and 7.8% decreased to 2.8% respectively. A corresponding increase in the concentration of 2,6-dichloro-3-trichloromethyl pyridine was noted, i.e. 5.3% to 13.0%. The following reactions were therefore occurring at this stage of process:

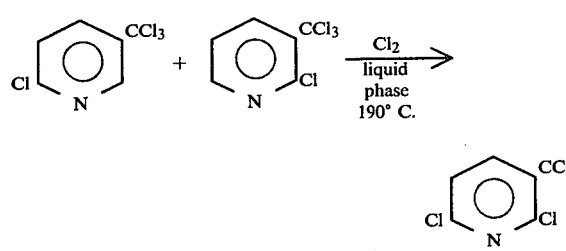

TABLE FIVE

| Compound | Initial Molar Concentration | Molar Concentration at 2 hrs of Chlorination at 190° C. |
| --- | --- | --- |
| 6-chloro-3-trichloromethyl pyridine | 15.6% | 9.6% |
| 2-chloro-3-trichloromethyl pyridine | 7.8% | 2.8% |
| 2,6-dichloro-3-trichloromethyl pyridine | 5.3% | 13.0% |

EXAMPLE 9

Example 9 shown in TABLE SIX illustrates an additional chlorination reaction occuring in this liquid phase system, namely:

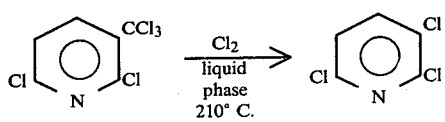

One hundred grams of a mixture rich in 6-chloro- and 2,6-dichloro-3-trichloromethyl pyridine were chlorinated for 4 hours in the liquid phase at 210° C. The 6-chloro-3-trichloromethyl pyridine concentration decreased from 6.9% to 2.1% during this time, while the 2,6-dichloro-3-trichloromethyl pyridine concentration increased only slightly from 12.9% to 14.3%. Concentration of 2,3,6-trichloro pyridine increased from 2.3% to 6.3%.

TABLE SIX

| Compound | Initial Molar Concentration | Molar Concentration at 4 hrs at Chlorination at 210° C. |
| --- | --- | --- |
| 6-chloro-3-trichloromethyl pyridine | 6.9% | 2.1% |
| 2-chloro-3-trichloromethyl pyridine | 0.9% | |
| 2,6-dichloro-3-trichloromethyl pyridine | 12.9% | 14.3% |
| 2,3,6-trichloro pyridine | 2.3% | 6.3% |

EXAMPLE 10

Liquid chlorination of a mixture rich in 2,3,6-trichloro pyridine catalyzed with four weight percent ferric chloride is illustrated in TABLE SEVEN and Example 10. Fifty grams of a mixture rich in 2,3,6-trichloro pyridine was chlorinated at 195° C. for 4 ¼ hours. The concentration of 2,3,6-trichloro pyridine decreased from 89.4% to 1.7% while the concentration of 2,3,5,6-tetrachloro pyridine increased from 4.5% to 97.6%.

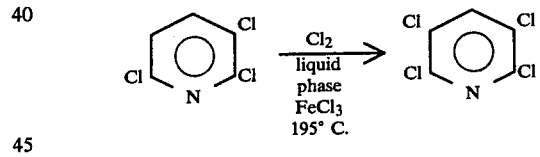

TABLE SEVEN

| Compound | Initial Molar Concentration | Molar Concentration after 9.25 hrs at 195° C. + 4% FeCl₃ |
| --- | --- | --- |
| 2,3,6-trichloro pyridine | 89.4% | 1.7% |
| 2,3,5,6-tetrachloro pyridine | 4.5 | 97.6 |
| pentachloro pyridine | | 0.6 |

It has been demonstrated by Examples 8-10 that various liquid phase, uncatalyzed and catalyzed chlorinations result in a method of producing mixtures rich in 2,3,5,6-tetrachloro pyridine, if desired. Useful chlorinated pyridines such as 6-chloro-3-trichloromethyl pyridine, may be separated out by vacuum distillation prior to being further chlorination, if desired.

EXAMPLE 11

This example illustrates the conversion of 5-chloro-3-trichloromethyl pyridine to 5,6-dichloro-3-trichloromethyl pyridine by liquid phase chlorination.

One hundred grams of a mixture rich in 5-chloro- and 5,6-dichloro-3-trichloromethyl pyridine was chlorinated in the liquid phase to a mixture richer in 5,6-dichloro-3-trichloromethyl pyridine and in 2,5,6-trichloro-3-trichloromethyl pyridine. TABLE EIGHT illustrates the results.

TABLE EIGHT

| Compound | Initial Molar Concentration | Molar Concentration after 3 hrs liquid phase chlorination @ 190° C. |
|---|---|---|
| 5-chloro-3-trichloromethyl pyridine | 4.7% | |
| 5,6-dichloro-3-trichloromethyl pyridine | 4.6 | 7.6% |
| 2,5,6-trichloro-3-trichloromethyl pyridine | 0.7 | 1.9 |

5-chloro-3-trichloromethyl pyridine $\xrightarrow[\text{190° C.}]{\text{Cl}_2 \text{ liquid phase}}$ 5,6-dichloro-3-trichloromethyl pyridine 5,6-dichloro-3-trichloromethyl pyridine $\xrightarrow[\text{190° C.}]{\text{Cl}_2 \text{ liquid phase}}$ 2,5,6-trichloro-3-trichloromethyl pyridine

EXAMPLE 12

970 grams of a mixture rich in 5,6-dichloro- and 2,5,6-trichloro-3-trichloromethyl pyridine were charged to a chlorinator. 200 grams per hour of chlorine were sparged into the bottom of the chlorinator for 8 hours at a reaction temperature of 260° C. and for 3 hours at a reactor temperature of 230° C. The 5,6-dichloro-3-trichloromethyl pyridine content decreased from 10.6 mole percent to 4.3 mole percent, while 2,5,6-trichloro-3-trichloromethyl pyridine content decreased from 19.1 mole percent to 9.2 mole percent. The 2,3,5,6-tetrachloro pyridine content of the mass increased from 28.5 mole percent to 44.2 mole percent.

In summary:

5,6-dichloro-3-trichloromethyl pyridine $\xrightarrow{\text{Cl}_2}$ 2,5,6-trichloro-3-trichloromethyl pyridine $\xrightarrow{\text{Cl}_2}$ 2,3,5,6-tetrachloro pyridine

|  | 5,6-dichloro-3-CCl₃ | 2,5,6-trichloro-3-CCl₃ | 2,3,5,6-tetrachloro | total moles |
|---|---|---|---|---|
| Start | 10.6% | 19.1 | 28.5 | 58.2 |
| Finish | 4.3 | 9.2 | 44.2 | 57.7 |

The above reactions occur during the production of 2,3,5,6-tetrachloro pyridine from 5,6-dichloro-3-trichloromethyl pyridine via 2,5,6-trichloro-3-trichloromethyl pyridine.

Examples 13 through 15 are presented to illustrate the fact that 2,5,6-trichloro-3-trichloromethyl pyridine can be prepared from 6-chloro-3-trichloromethyl pyridine or from 2,6-dichloro-3-trichloromethyl pyridine as well as from 5,6-dichloro-3-trichloromethyl pyridine (as described in Examples 11 and 12). Regardless of the method of preparation of 2,5,6-trichloro-3-trichloromethyl pyridine, non-catalytic liquid phase chlorination thereof at temperatures in excess of 190° C. yields mixtures rich in 2,3,5,6-tetrachloro pyridine.

EXAMPLE 13

Seventy-five grams of a chlorinated pyridine mixture containing 79.2 mole percent 6-chloro-3-trichloromethyl pyridine was chlorinated catalytically as suggested by Ishihara Sangyo Kaisha Ltd. in Japan Kokai Tokkyo Koho 82,183,760 (Chem. Abs., 98:143281b (1983)).

Thus, two grams of ferric chloride were added to the above mentioned chlorinated pyridine mixture and chlorine was fed (sparged) into the liquid at 70 grams per hour and at temperatures from 200° C. to 215° C. The reaction temperature can be as low as 160° C. The catalyst can be a halide of Fe, W, Mo, Ti, or Sb.

The data in TABLE NINE illustrate that 2,5,6-trichloro-3-trichloromethyl pyridine can be made from 6-chloro-3-trichloromethyl pyridine by way of 5,6-dichloro- or 2,6-dichloro-3-trichloromethyl pyridine.

TABLE NINE

| Compound | Initial Molar Concentration | Molar Concentration after 6 hrs of chlorination at 200° C. | Molar Concentration after 12 hrs of chlorination at 200° C. | Molar Concentration after 12 hrs of chlorination at 200° C. and 15 hrs of chlorination at 215° C. |
|---|---|---|---|---|
| 2,3,6-trichloropyridine | | 2.2% | 2.7% | 1.0% |
| 2,3,5,6-tetrachloropyridine | 18.6% | 17.6 | 18.4 | 24.8 |
| 2-chloro-3-trichloromethyl pyridine (Cl, CCl₃) | 79.2 | 38.8 | 25.4 | 3.1 |
| pentachloropyridine | 0.6 | 2.3 | 3.2 | 5.5 |
| 2,3-dichloro-6-trichloromethyl pyridine | | 12.0 | 15.3 | 20.4 |
| 2,6-dichloro-3-trichloromethyl pyridine | | 19.0 | 18.7 | 4.1 |
| 2,3,5-trichloro-6-trichloromethyl pyridine (or 2,5,6-trichloro-3-trichloromethyl) | | 5.6 | 13.5 | 36.8 |

EXAMPLE 14

Continued chlorination of 5,6-dichloro- and 2,5,6-trichloromethyl pyridine using a catalyst does not give optimum results. Therefore, the chlorinated pyridine product made in Example 13 (after chlorination for 12 hours at 200° C. and 15 hours at 215° C.) was water washed four times with two volumes of fresh water per volume of chlorinated pyridine product in order to remove the catalyst ferric chloride. (Distillation is another method that can be used to separate the chloropyridine from the ferric chloride.)

The resulting ferric chloride-free product was then non-catalytically chlorinated in liquid phase at 260° C. for 6 hours in a mechanically agitated reactor with a chlorine flow of 7 grams per hour. The reaction temperature can be as low as 190° C. The bulk of the 2,5,6-trichloro-3-trichloromethyl pyridine was converted to 2,3,5,6-tetrachloro pyridine as can be seen in TABLE TEN.

TABLE TEN

| Compound | Initial Molar Concentration | Molar Concentration After 6 hrs Clorination at 260° C. |
|---|---|---|
| 2,3,6-trichloropyridine | 1.0% | 5.7% |
| 2,3,5,6-tetrachloropyridine | 24.8 | 56.0 |
| 2-chloro-3-trichloromethyl pyridine | 3.1 | — |

TABLE TEN-continued

| Compound | Initial Molar Concentration | Molar Concentration After 6 hrs Clorination at 260° C. |
|---|---|---|
| Cl, Cl, Cl, Cl pyridine (tetrachloro) | 5.5 | 7.8 |
| Cl, Cl, CCl₃ pyridine | 20.4 | 8.5 |
| Cl, CCl₃, Cl pyridine | 4.1 | 2.9 |
| Cl, Cl, CCl₃, Cl pyridine | 36.8 | 19.0 |

EXAMPLE 15

Seventy-five grams of a chloropyridine mixture containing 88.1 mole percent 2,6-dichloro-3-trichloromethyl pyridine were chlorinated in a mechanically agitated chlorinator with a chlorine flow of 10 grams per hour at 220° C. after 3 grams of ferric chloride were added to the mixture. The reaction temperature can be as low as 160° C. TABLE ELEVEN shows that after 3½ hours of chlorination, the 2,6-dichloro-3-trichloromethy pyridine had essentially been completely converted to 2,5,6-trichloro-3-trichloromethyl pyridine at 72.5 percent molar concentration or its further chlorinated product 2,3,5,6-tetrachloro pyridine at 22.0 percent molar concentration. This is added proof that 2,5,6-trichloro-3-trichloromethyl pyridine can be made from 2,6-dichloro-3-trichloromethyl pyridine.

At this point, the chlorinated pyridine product made in Example 15 may be treated according to the first step in Example 14 to remove the catalyst ferric chloride. The catalyst-free product may then be non-catalytically chlorinated according to the second step in Example 14 to convert the bulk of the 2,5,6-trichloro-3-trichloromethyl pyridine to 2,3,5,6-tetrachloro pyridine.

When the batch is further chlorinated for 4 additional hours at 220° C. without removing the ferric chloride catalyst, the results are shown in TABLE ELEVEN. The concentration of 2,3,4,5,6-pentachloro pyridine increased to 24.2 mole percent and the concentration of 2,5,6-trichloro-3-trichloromethyl pyridine decreased to 35.4 mole percent. Therefore the bulk of the 2,5,6-trichloro-3-trichloromethyl pyridine does not go exclusively to 2,3,5,6-tetrachloro pyridine, but also makes significant quantities of 2,3,4,5,6-pentachloro pyridine. This is undesirable from an efficient yield standpoint.

TABLE ELEVEN

| Compound | Initial Molar Concentration | Molar Concentration after 3½ hrs @ 220° C. | Molar Concentration after 7½ hrs total @ 220° C. |
|---|---|---|---|
| Cl, Cl, Cl pyridine | — | — | — |
| Cl, Cl pyridine | 1.6% | 22.0% | 34.9% |
| CCl₃, Cl pyridine | 88.1 | 0.9 | 0.9 |
| Cl, CCl₃, Cl pyridine | 6.1 | 72.5 | 35.4 |
| Cl, Cl, Cl pyridine | — | 2.1 | 24.2 |

EXAMPLE 16

Eighty-five grams of a mixture rich in 2,3,6-trichloro pyridine and 2,6-dichloro-3-trichloromethyl pyridine were chlorinated without catalyst for 14 hours at 225° C. using mechanical agitation and a feed rate of 15 grams per hour of chlorine. The 2,3,6-trichloro pyridine molar concentration initially was 30.6 mole percent. After the 14 hours of chlorination, it had increased to 53.4 mole percent. The 2,6-dichloro-3-trichloromethyl pyridine concentration was initially 61.1 mole percent. Then, after the 14 hours of chlorination it decreased to 26.8 mole percent. 2,3,5,6-tetrachloro pyridine was initially present at 2.5 mole percent. After the 14 hours of chlorination its molar concentration had increased to 12.5%. 2,3,5,6-tetrachloro pyridine was, therefore, the product of non-catalytic chlorination of 2,3,6-trichloro pyridine. The reaction temperature can be as low as 190° C.

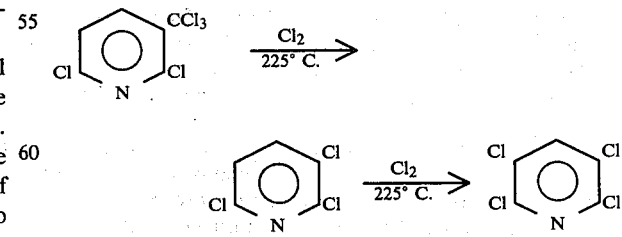

The 2,3,6-trichloro pyridine can be separated from the mixture by distillation and then treated as in Example 10 to form 2,3,5,6-tetrachloro pyridine by catalytic chlorination.

EXAMPLE 17

Sixty-five grams of a mixture rich in 2,3,6-trichloro pyridine were chlorinated without catalyst at a feed rate of 15 grams per hour of chlorine using mechanical agitation. The 2,3,6-trichloro pyridine molar concentration initially was 96.3 mole percent. The 2,6-dichloro pyridine concentration initially was 1.6 mole percent. The 2,3,5,6-tetrachloro pyridine concentration initially was 1.5 mole percent. The mixture was chlorinated for 5 hours at 200° C., for 5 hours at 210° C., for 4 hours at 220° C., and for 4 hours at 230° C. (total: 18 hours). After the 18 hours of chlorination, the 2,3,6-trichloro pyridine concentration decreased to 94.3 mole percent. The 2,6-dichloro pyridine concentration decreased to 0.9 mole percent. The 2,3,5,6-tetrachloro pyridine concentration increased to 4.1 mole percent. The reaction temperature can be as low as 190° C., but the rate of reaction will be very low unless the chlorination is conducted under high pressure conditions, such as 300 pounds of chlorine pressure.

In composite, the foregoing Examples 8 through 10 demonstrate that liquid phase chlorination carried out at a temperature of at least about 190° C. while feeding chlorine into a reactor charge progressively converts 2-chloro-3-trichloromethyl pyridine and/or 6-chloro-3-trichloromethyl pyridine to 2,6-dichloro-3-trichloromethyl pyridine, which then converts to 2,3,6-trichloro pyridine and then in turn to 2,3,5,6-tetrachloro pyridine. Such conversion may be selectively controlled to be on a substantially quantitative basis, or can produce some intermediate mixture, depending on the time the chlorination is maintained.

Similarly, Examples 11 and 12 demonstrate that chlorination under like conditions of mixtures rich in 5-chloro-3-trichloromethyl pyridine and 5,6-dichloro-3-trichloromethyl pyridine forms mixtures richer in 5,6-dichloro-3-trichloromethyl pyridine, along with further conversion thereof to 2,5,6-trichloro-3-trichloromethyl pyridine, the 2,5,6-trichloro-3-trichloromethyl pyridine being converted in turn to 2,3,5,6-tetrachloro pyridine.

Example 13 demonstrates that catalytic liquid phase chlorination carried out at a temperature of at least about 160° C. while feeding chlorine into a reactor charge converts mixtures rich in 6-chloro-3-trichloromethyl pyridine to mixtures rich in 5,6-dichloro- and 2,5,6-trichloro-3-trichloromethyl pyridine. Example 14 demonstrates that non-catalytic liquid phase chlorination carried out at a temperature of at least about 190° C. while feeding chlorine into a reactor charge converts mixtures rich in 5,6-dichloro- and 2,5,6-trichloro-3-trichloromethyl pyridine to mixtures rich in 2,3,5,6-tetrachloro pyridine. Example 15 shows that catalytic liquid phase chlorination carried out at a temperature of at least about 160° C. while feeding chlorine into a reactor charge converts mixtures rich in 2,6-dichloro-3-trichloromethyl pyridine to mixtures rich in 2,5,6-trichloro-3-trichloromethyl pyridine. Example 16 shows that non-catalytic chlorination of mixtures rich in 2,3,6-trichloro pyridine and 2,6-dichloro-3-trichloromethyl pyridine result in mixtures rich in 2,3,6-trichloro pyridine and 2,3,5,6-tetrachloro pyridine. Example 17 shows that a mixture rich in 2,3,6-trichloro pyridine can be non-catalytically chlorinated to form 2,3,5,6-tetrachloro pyridine.

Such an extent of conversion of these monochloro and dichloro-3-trichloromethyl pyridines to the indicated dichloro-and trichloro-3-trichloromethyl pyridines and the indicated trichloro and tetrachloro pyridines by direct chlorination is considered unique and provides valuable intermediates for subsequent manufacture of herbicides and insecticides by a much simpler and more straightforward process than heretofore known.

The reaction mechanism involved in the liquid phase chlorination of beta-picoline appears to be such that at temperatures less than about 190° C. in the primary reactor 2,4,6-trichloro-3-trichloromethyl pyridine is formed, by a progression from the monochloro trichloromethyl to the dichloro trichloromethyl and then to the trichloromethyl, with the final product being 2,4,6-chloro-3-trichloromethyl pyridine, for which there is no known utility. Yield averages in the temperature range from 100° C. to about 180° C. prove to be from 60% to 70%, so reaction products at primary reactor temperatures less than 190° C. do not appear to have much utility. We have now discovered, however, that at primary reactor R1 temperatures from 190° C. up to higher liquid phase chlorination temperatures, e.g., 250° C., a whole series of useful reaction products is realized, and at temperatures about 220° C. and above there is very little 2,4,6-trichloro-3-trichloromethyl pyridine formed. Typical product compositions at 220° C. and higher reaction temperatures in the primary reactor involve about 10% 5-chloro-3-trichloromethyl pyridine, 40% 6-chloro-3-trichloromethyl pyridine, 20% 2-chloro-3-trichloromelthyl pyridine by weight and smaller amounts on the order of 1 to 2% of the 5,6-dichloro-3-trichloromethyl pyridine and the 2,6-dichloro-3-trichloromethyl pyridine.

As earlier indicated, we have also discovered that these products can be further chlorinated non-catalytically, at predictable functions of time vs. temperature, to give other useful intermediates. For example, when subjected to further non-catalytic chlorination in liquid phase at high temperature, 5-chloro-3-trichloromethyl pyridine goes to 5,6-dichloro-3-trichloromethyl pyridine. Similarly 6-chloro-3-trichloromethyl pyridine non-catalytically chlorinates to 2,6-dichloro-3-trichloromethyl pyridine as does 2-chloro-3-trichloromethyl pyridine. The process can be interrupted at this stage and these two main components, namely, 5,6-dichloro-3-trichloromethyl pyridine and 2,6-dichloro-3-trichloromethyl pyridine, may be separated out, or, if chlorination is continued, 5,6-dichloro-3-trichloromethyl pyridine goes to 2,5,6-trichloro-3-trichloromethyl pyridine and on still further chlorination to 2,3,5,6-tetrachloro pyridine, which has great utility as an intermediate in insecticidal compositions. 2,6-dichloro-3-trichloromethyl pyridine can be chlorinated non-catalytically further to 2,3,6-trichloro pyridine. In addition, 5,6-dichloro-, 2,6-dichloro-, and 2,5,6-trichloro-3-trichloromethyl pyridine can be prepared by catalytic chlorination of 6-chloro-3-trichloromethyl pyridine. Also, 2,5,6-trichloro-3-trichloromethyl pyridine can be prepared by catalytic chlorination of 2,6-dichloro-3-trichloromethyl pyridine. Removal of the catalyst from 5,6-dichloro-, 2,6-dichloro-, and/or 2,5,6-trichloro-3-trichloromethyl pyridine will allow the above mentioned non-catalytic chlorination to proceed to the final chlorination products, namely, 2,3,6-trichloro pyridine and 2,3,5,6-tetrachloro pyridine. The 2,3,6-trichloro pyridine also can be chlorinated with or without ferric chloride catalyst to 2,3,5,6-tetrachloro pyridine. The ferric chloride catalyzed reaction is a much faster and therefore more economical route to 2,3,5,6-tetrachloro pyridine from 2,3,6-trichloro pyridine. The process can be selectively controlled to realize a very high yield of 2,3,5,6-tetrachloro pyridine, or the yield of 5,6-dichloro-3-trichloromethyl pyridine and 6-chloro-3-trichloromethyl pyridine, both of which have utility as intermediates for herbicides, can be maximized by not chlorinating as long.

In general, the primary reactor R1 is maintained at a temperature of at least 190°. Its maximum practical temperature for practice of the present invention is that temperature at which it can be safely operated in the liquid phase. Retention time in the primary reactor R1 should also be such that there is no unreacted beta picoline or beta picoline hydrochloride in vent line 26 or in the liquid passed to the secondary reactor R2 through line 34. In what is considered the best mode for practice of the invention (Example 1), the secondary reactor R2 is maintined at 150° C. This relatively low temperature in reactor R2 serves two purposes. It effectively slows the reaction down so further chlorinations are controlled and the desired end point is not overshot. In addition, the lower temperature in R2 helps to absorb and quench the very hot overhead vapor from reactor R1 and makes it easier for absorber C2 to be maintained at its relatively low operating temperature (140° C.), so that it will effectively of keep the high melting point pyridines from being carried over into scrubbing column C1 and plugging it up. Secondary reactor R2, when operated at a temperature substantially lower than the primary reactor R1, serves as what might be termed a buffering or stabilizer reactor. It need not be cooler than reactor R1, however. It all depends on what end products are desired.

Finishing reactors R3A and R3B are also run at a selected temperature, 210° C. in the case of Example 1, and a selected time, 12 hours in Example 1, to get a maximum composition of the desired products, e.g. in Example 1 to get 6-chloro- and 5,6-dichloro-3-trichloromethyl pyridine and the derivatives that go to 2,3,6-trichloro pyridines on further chlorination. If the reaction objective is to make a product rich in 2,3,6-trichloro pyridine and 2,3,5,6-trichloro pyridine, secondary reactor R2 should be run very hot and the finishing reactors R3A and R3B also should be run very hot for a very long period of time, since these final products are "at the end of the line", from the point of view of progressive chlorination reaction.

The main criteria for the absorbent charge in absorber C2 is that it is nonreactive at the temperature at which the absorber operates (140° C.), is a compound or mixture of compounds having a melting point less than 80° C., and is mutually soluble in carbon tetrachloride so that it doesn't plug up the scrubbing column C1, either through melting or freezing or lack of solubilization. The absorber charge, being nonreactive, is basically is a one time charge and recycled after removal of the absorbed product components, with only slight makeup from time to time. Functionally, the absorbent acts and is handled in much the same way as the carbon tetrachloride in the scrubbing column C1.

The chlorination process described in Taplin U.S. Pat. No. 3,424,754 relies on chlorine gas sparging into the liquid reaction mass to dissolve the chlorine in the reaction mass and to mix alpha-picoline hydrochloride with the initiator charge. According to Chemical Engineering Handbook, Perry, 3d Edition, page 1215 (1950), agitation produced by the degree of gas sparging involved in the process of U.S. Pat. No. 3,424,754 (estimated to be about 1.5 cubic foot per square foot minute at 200° C.) is usually too mild to move immiscible liquids with appreciable density differences into good contact with each other. In reactions according to the present invention, it is a practical necessity to maintain the reaction mass well mixed so that there is good contact and quick dispersion of the beta-picoline hydrochloride into the diluent at the desired reaction temperatures of greater than 190° C. because the polychlorinated pyridine diluent and the beta-picoline hydrochloride are immiscible and have substantially different densities (about 1.6 and about 1.2 grams per cubic centimeter, respectively), and because beta-picoline hydrochloride is unstable in this temperature range, i.e. the salt tends to break down to its components, namely hydrogen chloride and beta-picoline. If there is breakdown into the components, the hydrogen chloride is volatile and escapes through the vent system and beta-picoline builds up in a lighter liquid phase. Experimentation has shown that chlorinating beta-picoline hydrochloride in the absence of a diluent at a temperature in excess of 160° C. results in intractable mixtures of tars and polymers. Such tendency to form higher molecular weight reaction products increases at higher reaction temperatures.

Yields of volatile chlorinated picolines in excess of 99% and other new useful products are obtained when care is taken to ensure a high partial pressure of chlorine and sufficient mixing and quick dispersion of the beta-picoline or beta-picoline hydrochloride into a chlorine rich diluent which does not substantially compete for the available chlorine. This is accomplished by sparging chlorine (in excess of that needed for the reaction) and beta-picoline or beta-picoline hydrochloride at closely spaced locations near the bottom of the reactor means containing the polychlorinated pyridine diluent charge. The mixing required to ensure adequate contact between the liquids and gas can be achieved by high gas flow rate sparging, mechanical agitation, or a combination of both. High gas flow rates as described by Braulich, A.J.; Ch. E. Journal, Volume 11, No. 1, pp. 73-79, can achieve mixing of a magnitude almost equivalent to high power input mechanical mixing. Several disadvantages are inherent in the use of high gas flow rates, however. They are:

(a) high entrainment of the reactor liquids to the scrubber column C1 where they are scrubbed with carbon tetrachloride and must be recycled to the reaction system.

(b) a large volume of chlorine gas which must be purified, dried, and recycled.

Another mode of operation to enhance mixing is to combine mechanical agitation with chlorine gas and beta-picoline or beta-picoline hydrochloride sparging to achieve the desired degree of mixing and excess chlorine. High maintenance of mechanical seals and agitators are some of the disadvantages of such a mechanical agitation system.

An increase in reactor back pressure aids in increasing the chlorine concentration in the reaction liquid. The stoichiometric amount of chlorine reacted per unit of beta-picoline fed is greater than 3:1 by weight. Chlorine in excess of the stiochiometric requirement is considered essential to ensure that the beta-picoline or beta-picoline hydrochloride does not form undesirable tars and polymers. Therefore, weight ratios of at least about 5:1 of chlorine to beta-picoline being fed are deemed necessary in practice of the present process.

Care must be taken not to exceed the thermal stability of the diluent system. Diluents such as 6-chloro- or 5,6-dichloro-2-trichloromethyl pyridine can decompose vigorously at temperatures greater than 260° C.

What is claimed is:

1. The process of producing high yields of mixtures rich in chlorinated picolines/pyridines by non-catalytically chlorinating beta-picoline or beta-picoline hydrochloride in the liquid phase without substantial formation of intractable nonvolatiles, said process comprising:
   (a) establishing in a reactor means an anhydrous diluent reactor charge which is made up of chlorinated pyridine and/or picoline compounds, said diluent being essentially nonreactive with chlorine in the sense of forming one mole or less of hydrogen chloride per mole of diluent under the reaction conditions to which the reactants in the reactor means are subjected;
   (b) while maintaining the reactor charge in the liquid phase and at a temperature of at least about 190° C. to about 260° C., sparging chlorine and beta-picoline or beta-picoline hydrochloride into the reactor charge near the bottom thereof at a chlorine-to-picoline feed ratio of at least about 5:1 by weight and at a feed rate low enough so that any separation of the reactor charge into a second, lighter phase composed of unchlorinated beta-picoline hydrochloride is minimized and is in any event less than about 10% of the reactor charge by volume, the excess of chlorine being fed to the reactor charge relative to the amount of beta-picoline being fed thereto providing enhanced agitation of the reaction mass and sufficient chlorine to ensure that the chlorine partial pressure in the vapor space over the reactor charge is greater than 50%, such reaction conditions being maintained until substantial side-chain and nuclear substitution of chlorine in the beta-picoline or beta-picoline hydrochloride has occurred; and
   (c) continuing chlorine addition and maintaining the reaction mass in the liquid phase at a temperature of at least about 190° C. in a finishing reactor means until the desired extent of side-chain and nuclear substitution of chlorine in the beta-picoline or beta-picoline hydrochloride has occurred.

2. The process of claim 1, performed in a continuous batch mode and in a series of at least three reactors, with the first two reactors having initial, essentially inert diluent charges as in step (a) of claim 1, with the reaction conditions of step (b) of claim 1 being maintained in the first reactor, with excess chlorine, hydrogen chloride and entrained products being transferred by vent line and sparger from the first reactor to the second reactor, with overflow liquid products of chlorination being transferred from the first reactor to the second reactor, the volatile hydrochlorides being absorbed and reacted further in the second reactor, and with overflow liquid from the second reactor being transferred to a third, finishing reactor into which third reactor chlorine is sparged.

3. The process of claim 2, wherein the temperature in the second reactor is lower than the temperature in the first reactor and the temperature in the third reactor is at least equal to that of the first reactor.

4. The process of claim 2, comprising maintaining all reactors at a temperature of at least about 190° C.

5. The process of claim 2, comprising continuing chlorination in the third, finishing reactor until the reaction product comprises at least about 16% 5,6-dichloro-3-trichloromethyl pyridine by weight.

6. The process of claim 2, comprising continuing chlorination in the third, finishing reactor until the reaction product comprises at least about 25% 2,3,6-trichloropyridine by weight.

7. The process of claim 2, comprising continuing chlorination in the third, finishing reactor at a temperature of at least about 190° C., for a time to substantially quantitatively convert the 2-chloro-3-trichloromethyl pyridine and 6-chloro-3-trichloromethyl pyridine present to 2,6-dichloro-3-trichloromethyl pyridine and/or 2,3,6-trichloro pyridine.

8. The process of claim 7, comprising continuing chlorination of the reaction mass until substantially all 2,6-dichloro-3-trichloromethyl pyridine is converted to 2,3,6-trichloro pyridine.

9. The process of claim 2, comprising continuing chlorination in the third, finishing reactor at a temperature of at least about 190° C. for a time to convert at least most of the 5-chloro-3-trichloromethyl pyridine to 5,6-dichloro-3-trichloro pyridine present, and at least most of the 5,6-dichloro-3-trichloromethyl pyridine present to 2,5,6-trichloro-3-trichloromethyl pyridine and/or 2,3,5,6-tetrachloro pyridine.

10. The process of claim 9, comprising continuing chlorination of the reaction mass until at least most of the 2,5,6-trichloro-3-trichloromethyl pyridine is converted to 2,3,5,6-tetrachloro pyridine.

11. The process of claim 2, comprising subjecting the reaction mass to further liquid phase chlorination at a temperature of at least about 190° C. until substantial 2,3,6-trichloropyridine is formed, separating the 2,3,6-trichloropyridine, and subjecting the separated 2,3,6-trichloropyridine to further chlorination in the presence of ferric chloride catalyst to form substantial amounts of 2,3,5,6-tetrachloropyridine.

12. The process of claim 11, comprising continuing chlorination until the reaction product is principally 2,3,5,6-tetrachloropyridine.

13. The process of claim 2, comprising delivering the reaction mass overflow from the second reactor alternately to a third reactor and to a fourth reactor, and sparging chlorine into each of the third and fourth reactors alternately to further chlorinate the reaction mass in a batch manner.

14. The process of claim 2, comprising removing from the third reactor the reaction product formed by further chlorination therein, subjecting such reaction product to product purification by vacuum distillation or the like, and returning the purified volatiles to the third reactor or equivalent for further chlorination.

15. The process of claim 2, wherein the average residence time of the reaction mass in each reactor is from about 5 to about 40 hours and the average total cycle time in the reactors is about 10 to about 120 hours.

16. The process of claim 1, wherein the diluent charged to the reactor means is selected from the group consisting of 3-chloro-, 5-chloro-, 6-chloro-, 5,6-dichloro-, 3,5-dichloro-, 3,6-dichloro-, 3,4,5-trichloro- and 3,5,6-trichloro-2-trichloromethyl pyridine, 2-chloro-, 6-chloro-, 2,6-dichloro-3-trichloromethyl pyridine, 2,3,6-trichloro-, 2,3,5,6-tetrachloro- and 2,3,4,5,6-pentachloro pyridine, and mixtures thereof.

17. The process of claim 1, wherein the diluent charged to the reactor is made up essentially of the chlorinated pyridine/picoline products from a previous reaction.

18. The process of claim 1, wherein the reaction product includes substantial amounts of 2-chloro-3-trichloromethyl pyridine, 5-chloro-3-trichloromethyl pyridine, 6-chloro-3-trichloromethyl pyridine, 5,6-dichloro-3-trichloromethyl pyridine, and 2,6-dichloro-3-trichloromethyl pyridine.

19. The process of claim 1, wherein the reaction product comprises at least about 20% 5,6-dichloro-3-trichloromethyl pyridine, with the volatile content of the reaction mass being at least about 98%.

20. The process of claim 2, comprising sparging the gases vented from the first reactor to the second reactor, sparging gases from the second reactor to an absorber containing an absorbent having a melting point of less than about 80° C. and a substantial solubility with carbon tetrachloride, such absorbent being maintained at a temperture of about 140° C. and functioning to effectively liquify and remove any higher melting point chloropyridines from the gases sparged thereto, passing the gases vented from the absorber to a refluxing scrubber column maintained at a temperature of from about 30° C. to about 100° C., passing liquid overflow from the second reactor to the third, finishing reactor means for further chlorination, and sparging gases vented from said third reactor means into the absorbent contained in said absorber.

21. The process according to claim 20, wherein absorbent media contained in said absorber is selected from the group consisting of 6-chloro-,5,6,-dichloro-, 3,6-dichloro-, 3,5-dichloro-2-trichloromethyl pyridine, and mixtures thereof.

22. The process of claim 20, wherein the temperature of said first reactor is maintained at a temperature of at least about 190° C., the temperature of said second reactor is maintained at a temperature of from about 150° C. to about 180° C., the temperature of said absorber is maintained at about 140° C., and the temperature of said third, finishing reactor means is maintained at at least about 210° C.

23. The process of claim 22, wherein liquid outflow from said absorber is subject to removal of polychlorinated pyridines from the absorbent, followed by recycling of the absorbent to the said absorber.

24. A process of non-catalytically chlorinating mixtures rich in 2-chloro-3-trichloromethyl pyridine and/or 6-chloro-3-trichloromethyl pyridine to form mixtures rich in 2,6-dichloro-3-trichloromethyl pyridine and/or 2,3,6-trichloro pyridine, comprising:
  (a) establishing in a reactor means a reactor charge comprising a mixture rich in 2-chloro-3-trichloromethyl pyridine and/or 6-chloro-3-trichloromethyl pyridine; and
  (b) while maintaining the reactor charge in liquid phase at a temperature of at least about 190° C., feeding chlorine into the reactor charge for a sufficient time to non-catalytically convert the mixture rich in 2-chloro-3-trichloromethyl pyridine and/or 6-chloro-3-trichloromethyl pyridine to a mixture rich in 2,6-dichloro-3-trichloromethyl pyridine and/or 2,3,6-trichloro pyridine.

25. The process of claim 24, comprising continuing the non-catalytic chlorination of the reaction mass until substantially all of the 2,6-dichloro-3-trichloromethyl pyridine is converted to 2,3,6-trichloro pyridine.

26. A process of non-catalytically chlorinating mixtures rich in 5-chloro-3-trichloromethyl pyridine and/or 5,6-dichloro-3-trichloromethyl pyridine to form mixtures rich in 2,5,6-trichloro-3-trichloromethyl pyridine and/or 2,3,5,6-tetrachloro pyridine, comprising:
  (a) establishing in a reactor means a reactor charge comprising a mixture rich in 5-chloro-3-trichloromethyl pyridine and/or 5,6-dichloro-3-trichloromethyl pyridine; and
  (b) while maintaining the reactor charge in liquid phase at a temperature of at least about 190° C., feeding chlorine into the reactor charge for a sufficient time to non-catalytically convert the mixture rich in 5-chloro-3-trichloromethyl pyridine and/or 5,6-dichloro-3-trichloromethyl pyridine to a mixture rich in 2,5,6-trichloro-3-trichloromethyl pyridine and/or 2,3,5,6-tetrachloro pyridine.

27. The process of claim 26, comprising continuing the non-catalytic chlorination of the reaction mass until most of the 2,5,6-trichloro-3-trichloromethyl pyridine is converted to 2,3,5,6-tetrachloro pyridine.

28. A process of catalytically chlorinating mixtures rich in 6-chloro-3-trichloromethyl pyridine to form mixtures rich in 2,5,6-trichloro-3-trichloromethyl pyridine and 2,3,5,6-tetrachloro pyridine, comprising:
  (a) establishing in a reactor means a reactor charge comprising a mixture rich in 6-chloro-3-trichloromethyl pyridine and a sufficient amount of a catalyst selected from the group consisting of the halides of Fe, W, Mo, Ti, and Sb;
  (b) while maintaining the reactor charge in liquid phase at a temperature of at least about 160° C., feeding chlorine into the reactor charge for a sufficient time to catalytically convert the mixture rich in 6-chloro-3-trichloromethyl pyridine to a mixture rich in 5,6-dichloro- and 2,5,6-trichloro-3-trichloromethyl pyridine;
  (c) removing the catalyst; and
  (d) while maintaining the reactor charge in the liquid phase at a temperature of at least about 190° C., feeding chlorine into and agitating the reactor charge for a sufficient time to non-catalytically convert the mixture rich in 5,6-dichloro- and 2,5,6-trichloro-3-trichloromethyl pyridine to a mixture rich in 2,5,6-trichloro-3-trichloromethyl pyridine and 2,3,5,6-tetrachloro pyridine.

29. A catalytic process of chlorinating a mixture rich in 2,6-dichloro-3-trichloromethyl pyridine to form a mixture rich in 2,5,6-trichloromethyl pyridine and 2,3,5,6-tetrachloro pyridine comprising:
  (a) establishing in a reactor means a reactor charge comprising a mixture rich in 2,6-dichloro-3-trichloromethyl pyridine and a sufficient amount of a catalyst selected from the group consisting of the halides fo Fe, W, Mo, Ti, and Sb; and
  (b) while maintaining the reactor charge in liquid phase at a temperature of at least about 160° C., feeding chlorine into and agitating the reactor charge for a sufficient time to catalytically convert the mixture rich in 2,6-dichloro-3-trichloromethyl pyridine to a mixture rich in 2,5,6-trichloro-3-trichloromethyl pyridine and 2,3,5,6-tetrachloro pyridine.

30. The process of claim 29, comprising the additional steps of:
  (c) removing the catalyst; and
  (d) while maintaining the reactor charge in the liquid phase at a temperature of at least about 190° C., feeding chlorine into and agitating the reactor charge for a sufficient time to non-catalytically convert at least a substantial portion of the 2,5,6-trichloro-3-trichloromethyl pyridine in the rich mixture to 2,3,5,6-tetrachloro pyridine.

31. The process of claim 29 wherein the catalyst is ferric chloride.

32. A process of non-catalytically chlorinating mixtures rich in 2,6-dichloro-3-trichloromethyl pyridine and 2,3,6-trichloro pyridine to form mixtures rich in 2,3,6-trichloro pyridine and 2,3,5,6-tetrachloro pyridine, comprising:
   (a) establishing in a reactor means a reactor charge comprising a mixture rich in 2,6-dichloro-3-trichloromethyl pyridine and 2,3,6-trichloro pyridine; and
   (b) while maintaining the reactor charge in liquid phase at a temperature of at least about 190° C., feeding chlorine into and agitating the reactor charge for a sufficient time to non-catalytically convert the mixture rich in 2,6-dichloro-3-trichloromethyl pyridine and 2,3,6-trichloro pyridine to a mixture rich in 2,3,6-trichloro pyridine and 2,3,5,6-tetrachloro pyridine.

33. The process of claim 32, comprising the additional steps of:
   (c) separating the 2,3,6-trichloro pyridine from the mixture; and
   (d) catalytically chlorinating the 2,3,6-trichloro pyridine until substantially all of the 2,3,6-trichloro pyridine is converted to 2,3,5,6-tetrachloro pyridine.

34. The process of claim 33 wherein the catalyst is ferric chloride.

35. A process of non-catalytically chlorinating mixtures rich in 2,3,6-trichloro pyridine to form 2,3,5,6-tetrachloro pyridine, comprising:
   (a) establishing in a reactor means a reactor charge comprising a mixture rich in 2,3,6-trichloro pyridine; and
   (b) while maintaining the reactor charge in liquid phase at a temperature of at least about 190° C., feeding chlorine into and agitating the reactor charge for a sufficient time to non-catalytically convert the 2,3,6-trichloro pyridine to 2,3,5,6-tetrachloro pyridine.

36. The process of producing high yields of mixtures rich in chlorinated picolines/pyridines by non-catalytically chlorinating beta-picoline or beta-picoline hydrochloride in the liquid phase without substantial formation of intractable nonvolatiles, said process comprising:
   (a) establishing in a first and second reactor means an anhydrous diluent reactor charge which is made up of chlorinated pyridine and/or picoline compounds, said diluent being essentially nonreactive with chlorine in the sense of forming one mole or less of hydrogen chloride per mole of diluent under the reaction conditions to which the reactants in the first and second reactor means are subjected;
   (b) while maintaining the reactor charge in said first reactor means in the liquid phase and at a temperature of at least about 190° C. to about 260° C., sparging chlorine and beta-picoline or beta-picoline hydrochloride into the reactor charge near the bottom thereof at a chlorine-to-picoline feed ratio of at least about 5:1 by weight and at a feed rate low enough so that any separation of the reactor charge into a second, lighter phase composed of unchlorinated beta-picoline hydrochloride is minimized and is in any event less than about 10% of the reactor charge by volume, the excess of chlorine being fed to the reactor charge relative to the amount of beta-picoline being fed thereto providing enhanced agitation of the reaction mass and sufficient chlorine to ensure that the chlorine partial pressure in the vapor space over the reactor charge is greater than 50%, such reaction conditions being maintained until substantial side-chain and nuclear substitution of chlorine in the beta-picoline or beta-picoline hydrochloride has occurred;
   (c) transferring excess chlorine, hydrogen chloride, and entrained products by heated vent line and sparger from said first reactor means to said second reactor means;
   (d) transferring overflow liquid from said first reactor means to said second reactor means;
   (e) continuing chlorine addition and maintaining the reaction mass in the liquid phase at a temperature of about 150° C. to about 260° C. in said second reactor means;
   (f) transferring overflow liquid from said second reactor means to a third, finishing reactor means; and
   (g) continuing chlorine feed and heating of the reaction mass, without further beta-picoline or beta-picoline hydrochloride feed, in the liquid phase at a temperature of at least about 190° C. in the third, finishing reactor means until the desired extent of side-chain and nuclear substitution of chlorine in the beta-picoline or beta-picoline hydrochloride has occurred.

37. The process of claim 36, performed in a continuous batch mode and in a series of at least four reactors, with the first two reactors having essentially inert diluent charges as in step (a) of claim 38, with the reaction conditions of step (b) of claim 38 being maintained in the first reactor, the volatile hydrochlorides being absorbed and reacted further in the second reactor, and with overflow liquid from the second reactor being transferred to the third, finishing reactor or alternatively to a fourth reactor and with chlorine being sparged into said third or fourth reactor.

* * * * *